US009782221B2

(12) United States Patent
Srinivasan (10) Patent No.: US 9,782,221 B2
(45) Date of Patent: *Oct. 10, 2017

(54) TREATMENT USING LOW INTENSITY LASER THERAPY (71) Applicant: C Laser, Inc., Lebanon, IN (US)

(72) Inventor: Pattanam Srinivasan, Lebanon, IN (US)

(73) Assignee: C Laser, Inc., Lebanon, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/870,327

(22) Filed: Sep. 30, 2015

(65) Prior Publication Data

US 2016/0015997 A1  Jan. 21, 2016

Related U.S. Application Data

(63) Continuation of application No. 12/631,835, filed on Jan. 8, 2010, now Pat. No. 9,149,647.

(51) Int. Cl.
*A61B 18/20* (2006.01)
*A61B 18/22* (2006.01)
(Continued)

(52) U.S. Cl.
CPC .............. *A61B 18/22* (2013.01); *A61B 34/25* (2016.02); *A61B 90/00* (2016.02); *A61D 1/00* (2013.01);
(Continued)

(58) Field of Classification Search
CPC ....... A61N 5/06; A61N 5/0622; A61N 5/0601
(Continued)

(56) References Cited

U.S. PATENT DOCUMENTS

| 4,566,438 | A | * | 1/1986 | Liese | ................... | A61B 5/6848 |
| | | | | | | 600/129 |
| 4,959,063 | A | * | 9/1990 | Kojima | ................. | A61B 18/24 |
| | | | | | | 604/44 |

(Continued)

FOREIGN PATENT DOCUMENTS

| DE | 44 29 192 | 2/1996 |
| DE | 200 03 349 | 6/2000 |

(Continued)

OTHER PUBLICATIONS

"Local Anesthetic," Wikipedia, the free encyclopedia, downloaded from the internet on Nov. 27, 2012, 10 pages http://en.wikipedia.org/wiki/Local_anesthetic.

(Continued)

*Primary Examiner* — John R Downey
(74) *Attorney, Agent, or Firm* — Fish & Richardson P.C.

(57) ABSTRACT

Deep Tissue Low Intensity Laser Therapy or Treatment (DT-LILT) as described here is a novel methodology through which selective destruction of nociceptive (pain) nerves can be brought upon by a medical laser delivery system using the phenomenon of absorption and cell resonance. Using this method nerve cells that transmit pain can be selectively destroyed leaving the surrounding tissues intact as no heat is generated. The delivery system incorporates a fine needle through which a 703 nm (range 690 to 710) pulsed wave low intensity laser is delivered deep into the body, directly to the area of pain causing selective destruction of pain nerves. Laser devices based on this methodology should be used only by the physician or equivalent professional community since diagnosing and defining the area of pain is critical to providing successful pain relief.

18 Claims, 7 Drawing Sheets

(51) Int. Cl.
*A61D 1/00* (2006.01)
*A61B 90/00* (2016.01)
*A61N 5/06* (2006.01)
*A61B 34/00* (2016.01)
*A61B 18/00* (2006.01)
*A61B 17/00* (2006.01)
*A61N 5/067* (2006.01)

(52) U.S. Cl.
CPC .. *A61N 5/0601* (2013.01); *A61B 2017/00172* (2013.01); *A61B 2018/00434* (2013.01); *A61B 2018/00577* (2013.01); *A61B 2018/00642* (2013.01); *A61B 2018/00708* (2013.01); *A61B 2018/2005* (2013.01); *A61N 2005/067* (2013.01); *A61N 2005/0612* (2013.01); *A61N 2005/0626* (2013.01); *A61N 2005/0662* (2013.01)

(58) Field of Classification Search
USPC .................. 606/2, 3, 13–16; 607/88–94
See application file for complete search history.

(56) References Cited

U.S. PATENT DOCUMENTS

| | | | |
|---|---|---|---|
| 5,464,436 A * | 11/1995 | Smith | A61N 5/0616 606/13 |
| 5,514,126 A * | 5/1996 | Prescott | A61B 18/22 606/10 |
| 5,772,597 A | 6/1998 | Goldberger et al. | |
| 5,807,261 A | 9/1998 | Benaron et al. | |
| 6,080,148 A | 6/2000 | Damasco et al. | |
| 6,157,854 A * | 12/2000 | Haber | A61N 5/0619 600/427 |
| 6,267,779 B1 * | 7/2001 | Gerdes | A61N 5/0616 606/3 |
| 6,519,485 B2 | 2/2003 | Wiesmann et al. | |
| 6,663,659 B2 | 12/2003 | McDaniel | |
| 6,921,413 B2 * | 7/2005 | Mahadevan-Jansen | A61N 5/0601 128/898 |
| 6,942,658 B1 * | 9/2005 | Rizoiu | A61B 18/22 606/16 |
| 7,976,571 B2 | 7/2011 | Neuberger | |
| 2001/0056278 A1 * | 12/2001 | Nield | A61B 18/22 606/15 |
| 2002/0045922 A1 * | 4/2002 | Nield | A61B 18/22 607/89 |
| 2002/0182186 A1 | 12/2002 | Loeb | |
| 2003/0028147 A1 * | 2/2003 | Aves | A61B 17/3401 604/164.06 |
| 2003/0120267 A1 | 6/2003 | Kaufman et al. | |
| 2003/0212388 A1 * | 11/2003 | Ronn | A61N 5/0616 606/9 |
| 2003/0225331 A1 | 12/2003 | Diederich et al. | |
| 2004/0014199 A1 | 1/2004 | Streeter | |
| 2004/0082942 A1 * | 4/2004 | Katzman | A61B 18/24 606/15 |
| 2004/0111132 A1 * | 6/2004 | Shenderova | A61N 5/0616 607/88 |
| 2005/0049582 A1 | 3/2005 | DeBenedictis et al. | |
| 2005/0065577 A1 | 3/2005 | McArthur et al. | |
| 2005/0113658 A1 | 5/2005 | Jacobson et al. | |
| 2005/0182293 A1 | 8/2005 | Katzman | |
| 2005/0283148 A1 * | 12/2005 | Janssen | A61B 18/1477 606/34 |
| 2006/0206172 A1 * | 9/2006 | DiMauro | A61N 5/0601 607/88 |
| 2007/0162093 A1 | 7/2007 | Porter | |
| 2007/0179485 A1 | 8/2007 | Yeik et al. | |
| 2007/0185367 A1 * | 8/2007 | Abdou | A61N 5/1027 600/3 |
| 2007/0213792 A1 * | 9/2007 | Yaroslavsky | A61N 5/0613 607/100 |
| 2008/0027520 A1 | 1/2008 | Choi et al. | |
| 2008/0077198 A1 * | 3/2008 | Webb | A61N 5/0618 607/88 |
| 2008/0091249 A1 * | 4/2008 | Wang | A61N 5/0613 607/88 |
| 2008/0125836 A1 | 5/2008 | Streeter et al. | |
| 2008/0140023 A1 * | 6/2008 | McMillan | A61B 18/20 604/272 |
| 2008/0249517 A1 | 10/2008 | Svanberg | |
| 2009/0069673 A1 * | 3/2009 | Tapalian | A61B 5/0066 600/425 |
| 2009/0125036 A1 | 5/2009 | Bleich | |
| 2009/0299349 A1 | 12/2009 | Kubota et al. | |
| 2010/0016783 A1 * | 1/2010 | Bourke, Jr. | A61K 41/0057 604/20 |
| 2011/0218524 A1 | 9/2011 | Cattaneo | |
| 2011/0301581 A1 | 12/2011 | Thyzel | |
| 2013/0281839 A1 | 10/2013 | Jain et al. | |

FOREIGN PATENT DOCUMENTS

| | | |
|---|---|---|
| JP | 2009-207605 | 9/2009 |
| KR | 963 395 | 6/2010 |
| WO | WO 98/33557 | 8/1998 |
| WO | WO00-57804 | 10/2000 |
| WO | WO 01/62171 | 8/2001 |

OTHER PUBLICATIONS

Morgan & Mikhail, Clinical Anesthesiology, second edition, Chapter 18, Pain Management, pp. 274-280 (12 total pages).
Schenk et al.; Percutaneous Laser Disk Decompression: A Review of Literature; AJNR 27; Jan. 2006; www.ajnr.org.
Singh et al.; Percutaneous Lumbar Laser Disc Decompression: A Systematic Review of Current Evidence; Pain Physician 2009; 12:573-588 ISSN 1533-3159: www.painphysicianjournal.com.
Tsai et al.; Plasma-mediated ablation: an optical tool for submicrometer surgery on neuronal and vascular systems; Science Direct, Current Opinion in Biotechnology 2009, 20:1-10; www.sciencedirect.com.
Turgut et al.; Extensive Damage to the End-Plates as a Complication of Laser Discectomy an Experimental Study Using an Animal Model; Acta Neurochirurgical 1997; 139: 404-410.
International Search Report and Written Opinion in International Application No. PCT/US2015/025870, mailed Jul. 24, 2015, 9 pages.
PCT Notification of Transmittal of the International Search Report and the Written Opinion of the International Searching Authority, or the Declaration issued in PCT/US2011/064376 on Feb. 6, 2012, 7 pages.
PCT International Preliminary Report on Patentability for Application No. PCT/US2011/064376 dated Aug. 13, 2013, 7 pages.
PCT Notification of Transmittal of the International Search Report and the Written Opinion of the International Searching Authority, or the Declaration issued in PCT/US2011/066006 on Apr. 19, 2012, 7 pages.
PCT International Preliminary Report on Patentability for Application No. PCT/US2011/066006 dated Aug. 13, 2013, 7 pages.
European Office Action in Application No. 11858106.5, dated Sep. 2, 2014, 5 pages.
European Search Report in Application No. 11858106.5, dated Aug. 21, 2014, 3 pages.
European Search Report issued in Application No. 11858224.6 on Feb. 27, 2015, 3 pages.
Communication Pursuant to Article 94(3) EPC issued in EP 11858224.6 on Mar. 19, 2015, 5 pages.
Communication Pursuant to Article 94(3) EPC issued in EP 11858106.5, dated Nov. 10, 2015, 3 pages.
U.S. Non-Final Office Action for U.S. Appl. No. 12/631,835 dated Dec. 20, 2011, 12 pages.
U.S. Final Office Action for U.S. Appl. No. 12/631,835 dated Jun. 19, 2012, 19 pages.

(56) References Cited

OTHER PUBLICATIONS

U.S. Non-Final Office Action for U.S. Appl. No. 12/631,835 dated Sep. 4, 2012, 26 pages.
U.S. Final Office Action for U.S. Appl. No. 12/631,835 dated Mar. 14, 2013, 31 pages.
U.S. Non-Final Office Action for U.S. Appl. No. 12/631,835 dated Mar. 14, 2014, 30 pages.
U.S. Final Office Action for U.S. Appl. No. 12/631,835 dated Jan. 12, 2015, 23 pages.
U.S. Non-Final Office Action for U.S. Appl. No. 13/022,178 dated Dec. 20, 2011, 11 pages.
U.S. Non-Final Office Action for U.S. Appl. No. 13/022,178 dated Aug. 17, 2012, 13 pages.
U.S. Final Office Action for U.S. Appl. No. 13/022,178 dated Feb. 13, 2013, 14 pages.
U.S. Non-Final Office Action for U.S. Appl. No. 13/022,178 dated Jan. 30, 2014, 18 pages.
U.S. Final Office Action for U.S. Appl. No. 13/022,178 dated Jul. 17, 2014, 15 pages.
U.S. Non-Final Office Action for U.S. Appl. No. 13/022,178 on Apr. 23, 2015, 19 pages.
U.S. Non-Final Office Action for U.S. Appl. No. 13/329,596 dated Nov. 14, 2013, 16 pages.
U.S. Notice of Allowance in U.S. Appl. No. 13/329,596, dated Sep. 23, 2014, 10 pages.
U.S. Notice of Allowance in U.S. Appl. No. 13/329,596, dated Dec. 24, 2014, 14 pages.
U.S. Notice of Allowance in U.S. Appl. No. 12/631,835 , dated Jul. 9, 2015, 17 pages.
U.S. Final Office Action for U.S. Appl. No. 13/022,178 dated Sep. 24, 2015, 13 pages.
U.S. Notice of Allowance in U.S. Appl. No. 14/727,140, dated Oct. 26, 2015, 18 pages.

* cited by examiner

TREATMENT USING LOW INTENSITY LASER THERAPY

CROSS-REFERENCE TO RELATED APPLICATIONS

This application is a continuation of U.S. Pat. No. 12/631,835 filed Jan. 8, 2010, the contents of which are herein incorporated by reference.

This application is related to U.S. application Ser. No. 13/022,178, filed Feb. 7, 2011; U.S. application Ser. No. 13/329,596, filed Dec. 19, 2011, now U.S. Pat. No. 9,044,594; and U.S. application Ser. No. 14/727,140, filed Jun. 1, 2015, the contents of each are herein incorporated by reference.

TECHNICAL FIELD

This application relates to laser medical devices and its use in pain medicine.

BACKGROUND OF THE INVENTION

Low level laser therapy (LLLT), also known as photobiomodulation, cold laser therapy, and laser biostimulation, is a medical and veterinary treatment, which uses low-level lasers or light-emitting diodes to stimulate or inhibit cellular function. LLLT uses light sources such as lasers or LEDs to deliver light of certain wavelengths at certain intensities to affect tissue regeneration, inflammation, or pain. Existing deep tissue lasers today use heat generation to cause a non-selective action destroying non-specific tissue on contact.

SUMMARY

In general, one aspect of the subject matter described in this specification may include using a deep tissue low intensity laser (DT-LIL) capable of producing cell resonance within a nerve cell that can selectively cause destruction of the nerve cells without affecting the surrounding tissues. The deep tissue low intensity laser treatment (DT-LILT) selectively destroys nerve cells on contact using absorption and cell resonance. DT-LILT does not generate sufficient heat to destroy tissue, allowing selective destruction when nerve cells selectively absorb the DT-LILT wavelength. Thus, selective deep tissue low intensity laser ablation (DT-LILA) of the nerves, or deep tissue low intensity laser neuroablation (DT-LILNA) takes place.

The selection of laser wavelength may depend on the absorption characteristics of the nerve cells. Heat may or may not be generated as the selective destruction takes place by cell resonance rather than by heat coagulation. The use of deep tissue low intensity laser neuroablation (DT-LILNA) is described herein and is different from other medical or tissue lasers that use heat generation. Clinical applications include treating chronic pain, soft tissue injury, wound healing and nerve regeneration.

Definition of Terms:
 1. DT-LILT: Deep Tissue Low Intensity Laser Treatment or Therapy.
 2. DT-LIL: Deep Tissue Low Intensity Laser.
 3. DT-LILA: Deep Tissue Low Intensity Laser Ablation.
 4. DT-LILNA: Deep Tissue Low Intensity Laser Neuroablation.

BRIEF DESCRIPTION OF THE DRAWINGS

In the drawings, like reference numbers represent corresponding parts throughout.

DETAILED DESCRIPTION

Current deep tissue medical lasers are typically high intensity lasers, with output powers usually around 100 mW or above, that generate heat to destroy contact tissue using techniques such as hemo-coagulation. However, these deep tissue medical lasers lack sufficient selectivity or specificity to destroy contact tissue without causing collateral damage to surrounding tissue. Traditional low level laser therapy (LLLT) techniques also lack sufficient specificity. Current LLLT techniques use indirect pain relief techniques such as minimal heat generation, vasodilatation or metabolic changes. These lead to temporary pain relief because they do not destroy problematic pain nerves that cause long-term pain.

The deep tissue low intensity laser treatment (DT-LILT) disclosed in this application selectively destroys nerve cells on contact using the phenomenon of absorption and cell resonance. DT-LILT does not generate heat, or the heat generated is not sufficient to destroy tissues, therefore selective destruction is brought upon by cell resonance when the nerve cells selectively absorb the DT-LILT laser wavelength. By causing destruction of nerve cells in this manner, DT-LILT can provide long-term pain relief extending for many months.

Figure 1:
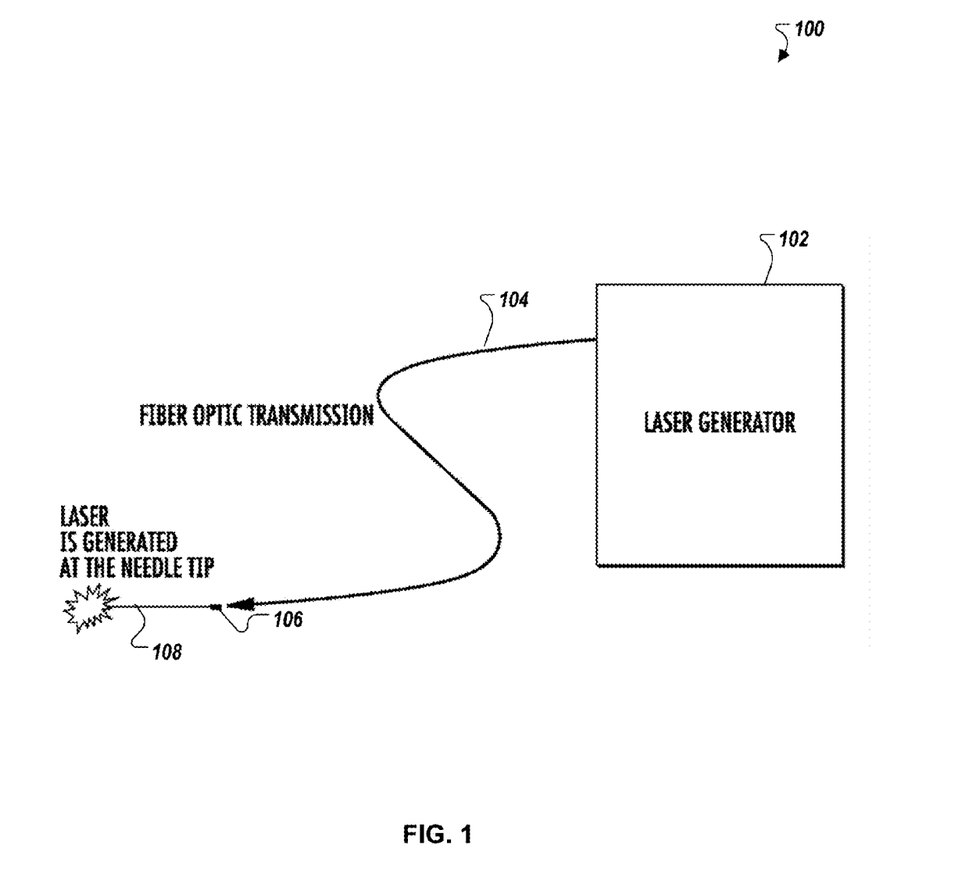
FIG. 1 illustrates a schematic diagram of an example laser delivery system for use with DT-LILT.

FIG. 1 illustrates a schematic diagram of an example laser delivery system 100 for use with DT-LILT. For example, the system 100 may include a laser generator 102, a laser fiber 104, a laser fiber fixator 106, and a needle 108. The system 100 may be used in DT-LILT by performing absorption and cell resonance to selectively destroy nerve cells without affecting the surrounding tissues.

In some implementations, the system 100 is used to specifically destroy nerve cells to provide long-term pain relief This is performed by causing absorption of specific wavelengths by nociceptive nerves when DT-LILT is directly applied to a pain generating area, bringing about the physiologic action of neuroablation (DT-LILNA) of the pain nerves. In such implementations, the DT-LILT may be minimally invasive and designed to be used within the pain generating area. For example, DT-LILT may be applied to specific areas of the spine as shown in FIGS. 3A-3G. The system 100 may be used to cause destruction of tissue without heat generation. For example, laser generator 102 may be a DT-LIL with power output less than 5 mW to allow deep tissue application. In some implementations, the DT-LIL may fall under laser classification 3R or below.

In one implementation, the system 100 includes the laser generator 102 capable of generating light of wavelength in the 690 nm to 710 nm range, the laser fiber 104 with diameters between 0.7 and 0.5 mm, and the laser fiber fixator 106 coupled with the needle 108 using a luer lock mechanism. The needle 108 may be a common Quincke spinal needle. The fixation between the laser fiber 104 and the spinal needle 108 can also be achieved by making the laser fiber and the spinal needle as one non detachable unit.

In some implementations, the laser generator 102 produces a laser with wavelength between 700 nm to 705 nm, laser output average power between 4 mW and 6 mW (with range between 1 mW and 6 mW), a laser pulsation at nanosecond or picosecond intervals, and timer controlled between 5 seconds and 10 seconds.

In some implementations, the nerve tissue consists of lipids that absorb the above laser wavelengths without impacting surrounding non-nervous tissue. For example, the laser generator 102 may have a wavelength between 690 nm and 710 nm with an optimal absorption at 703 nm, and with low output and high pulsation, which is absorbed by the nociceptive nerves. In such an example, using a 703 nm laser with the low output and high pulsation causes the nociceptive nerves to be selectively destroyed leaving surrounding tissue intact without heat generation.

In some implementations, the needle 108 is a fine needle that is 22G or smaller to deliver the laser treatment deep into the tissue. In some implementations, the needle 108 is 25G with a 0.5 mm inner diameter to fit a 300 µm laser fiber 104 and insert the laser fiber 104 below the body surface of a human patient. The fine needle 108 facilitates reaching tissue areas of treatment that may lie deep from the body surface and the inserted laser fiber facilitates the laser delivery to the area of treatment. In some implementations, the needle 108 may be a Quincke spinal needle. The fine needle 108 may provide cost savings as compared to heavier and bigger conduits for laser delivery.

In some instances, the design of the needle 108 includes laser fiber 104 embedded within the cannula of the needle to form a non-detachable unit. In some instances, the system 100 includes a laser fiber fixator 106 with a luer lock mechanism to facilitate the attachment of different-sized syringes to various sized needles. For example, the laser fiber fixator 106 with a luer lock mechanism may be used to attach the needle 108, which may be a Quincke spinal needle, to the laser fiber 104, which fixes the laser fiber within the needle and prevents movement of the fiber during laser delivery. In some implementations, the laser fiber fixator 106 includes a tuohy borst adapter with a blue cap and a male luer lock connector with a spin lock. In such implementations, the dimensions of the laser fiber fixator 106 may be between 2-6 FR (0.026 in-0.083 in) (0.66 mm-2.11 mm) (22-12 Gauge). In such implementations, the material of the laser fiber fixator 106 may be acrylic, polycarbonate, or silicone.

Figure 2:
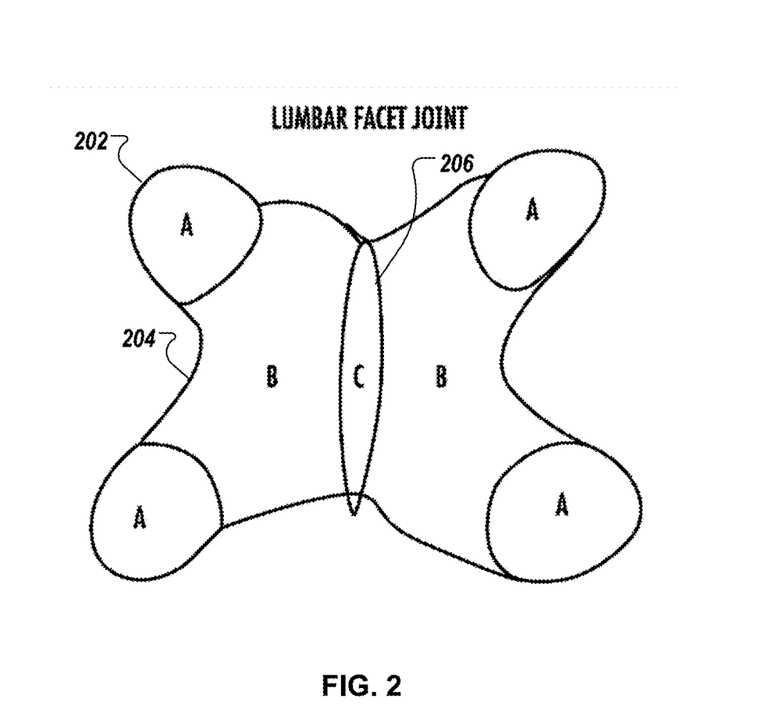
FIG. 2 illustrates an AP x-ray view of a lumbar facet joint, a lamina and a spinous process.

In some implementations, the system 100 may be used to perform a method that includes an intra-operative treatment using facet joint neuroablation, also known as medial branch neuroablation, as represented in FIG. 2. For example, the method may use a simple AP x-ray view and pass a deep tissue low intensity laser to cause a DT-LILNA. In another example, the DT-LIL may cause a DT-LILA. This is in contrast to conventional neuroablation that is based on finding the medial branch nerve in an oblique/lateral X ray view and using heat or chemical substance to destroy the medial branch.

FIG. 2 illustrates an AP X-Ray view of lumbar facet joints 202, a lamina 204 and a spinous process 206. DT-LILT may be applied to specific areas of the spine as shown in FIG. 2, using laser points as shown in FIGS. 3A-3G.

Although FIG. 2 shows the lumbar facet joint as laser points for the application of DT-LILT using the laser delivery system 100, the laser points used in DT-LILT are also applicable to all facet joints, including thoracic and cervical facet joints. When the size of the facet joint is smaller, the laser points and the laser area for DT-LILT may reduce but the pattern of laser delivery remains the same.

Figure 3A:
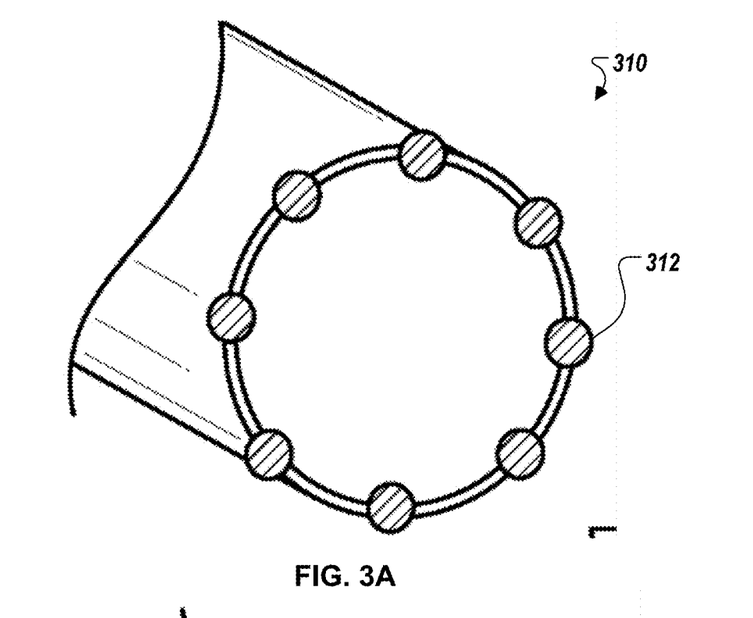
FIGS. 3A-3G illustrate single lumbar facet joints with various laser point configurations for DT-LILT.
Figure 3B:
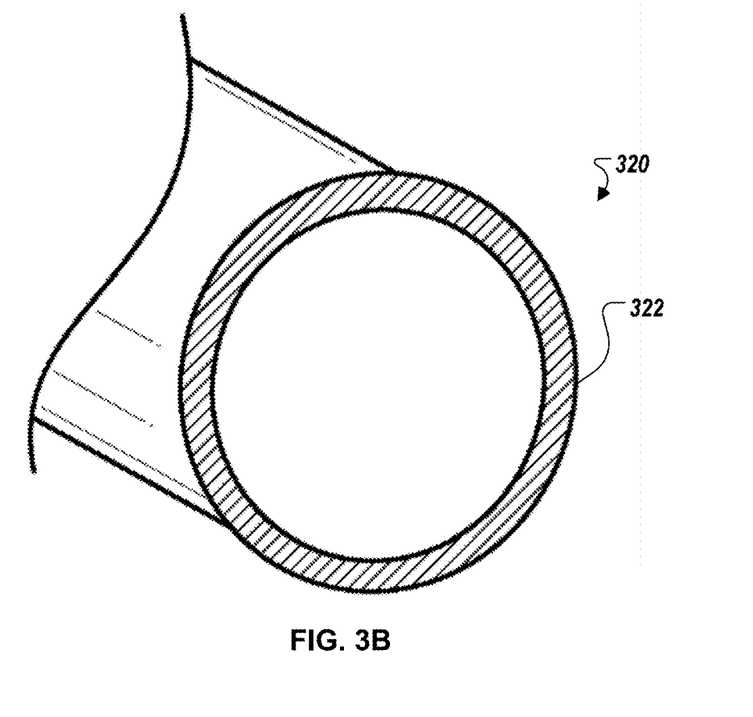
Figure 3C:
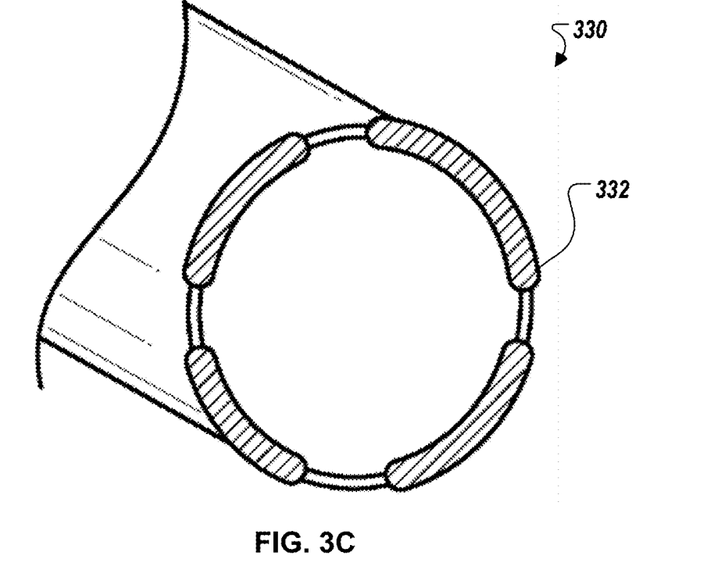
Figure 3D:
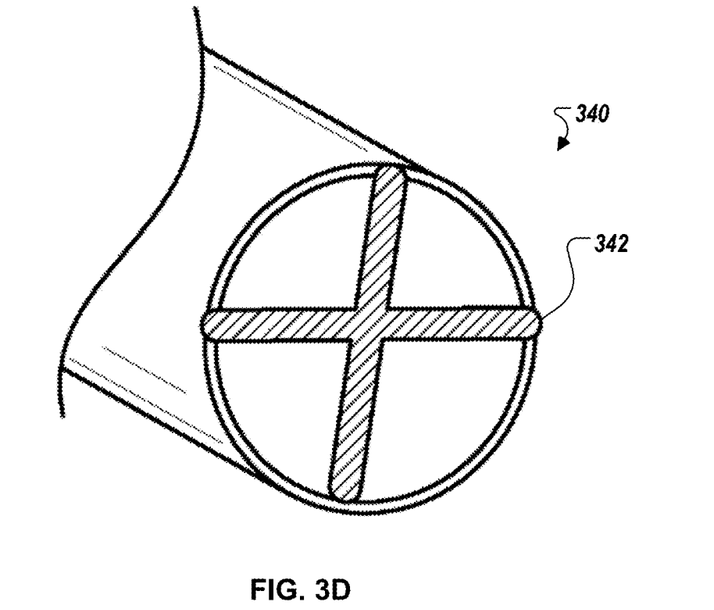
Figure 3E:
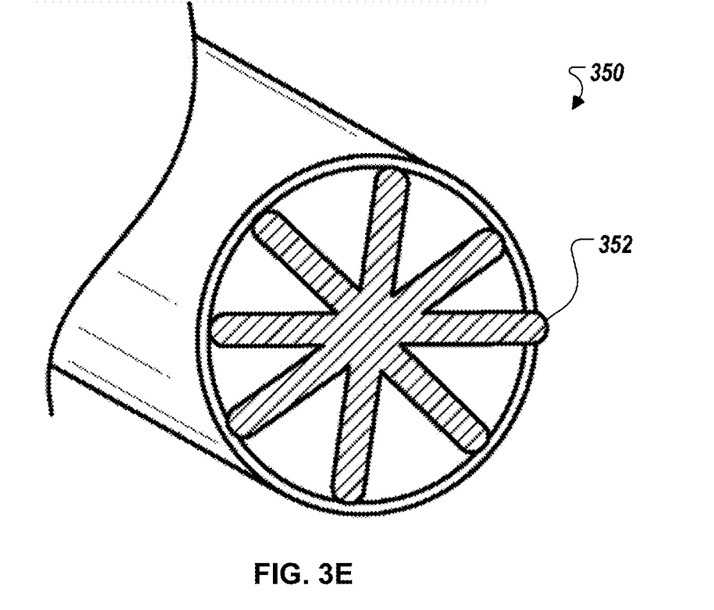
Figure 3F:
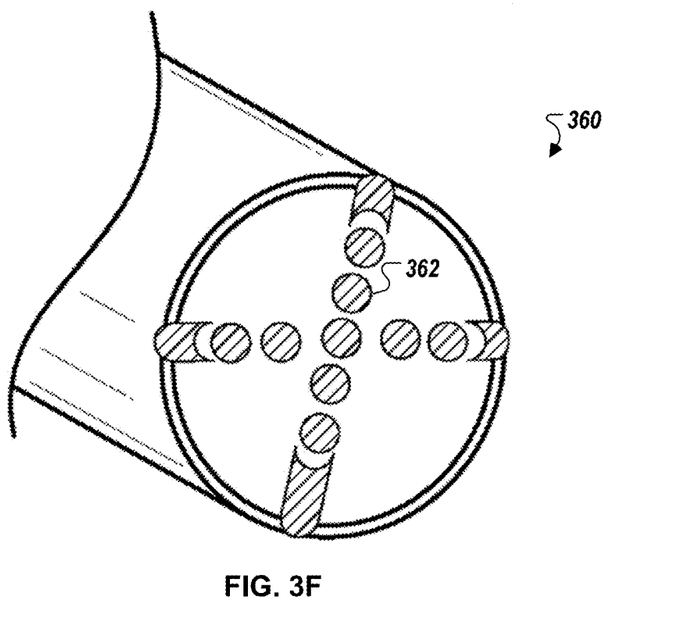
Figure 3G:
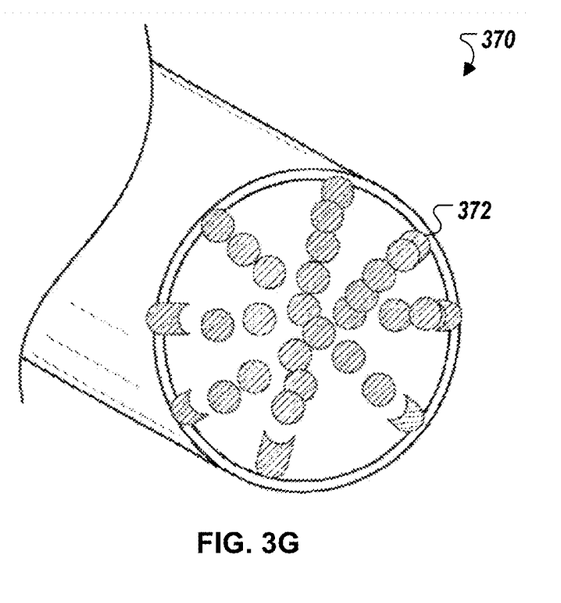

FIGS. 3A-3G illustrate single lumbar facet joints with various laser point configurations for DT-LILT. Referring to FIG. 3A, laser points 312 may be made in eight points in a circular fashion around the facet joint 310. Referring to FIG. 3B, laser points 322 may be made in a continuous circular fashion around the facet joint 320. Referring to FIG. 3C, the laser points 332 may be made in continuous intermittent fashion around the facet joint 330. Referring to FIG. 3D, the laser points 342 may be made in continuous cross fashion across the facet joint 340. Referring to FIG. 3E, the laser points 352 may be made in continuous multiple cross fashion across the facet joint 350. Referring to FIG. 3F, the laser points 362 may be made in continuous intermittent fashion 4 across the facet joint 360. Referring to FIG. 3G, the laser points 372 may be made in a continuous intermittent fashion multiple across the facet joint 370.

Figure 4:
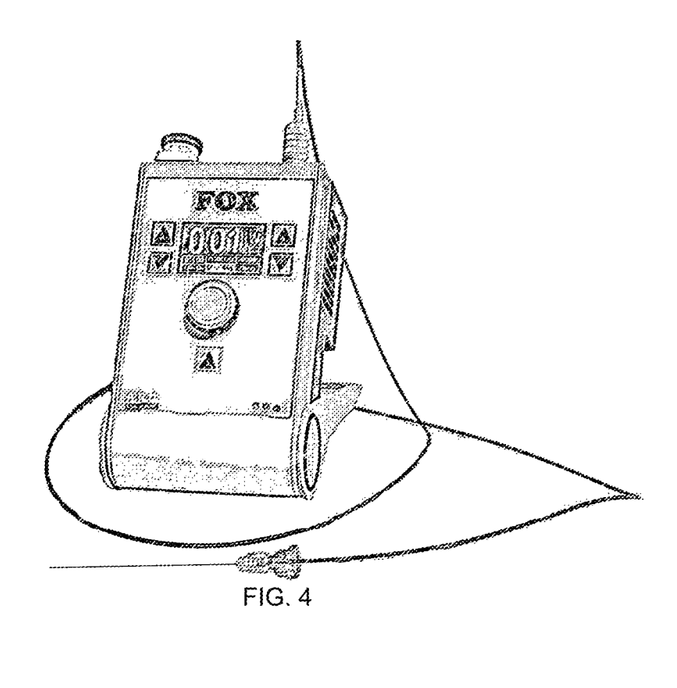
FIG. 4 illustrates an example laser delivery system for use with DT-LILT.

FIG. 4 illustrates an example laser delivery system 400 for use with DT-LILT. The laser delivery system 400 may be used for a medical procedure for treating reoccurring pain. In some implementations, the laser delivery system 400 is similar to the system 100.

In some implementations, the system 100 or the system 400 includes specified operating parameters for DT-LILT. For example, the laser generator 102 generates a 703 nm wavelength laser with 2 nm specified range, has an average 4 mW output power with a 0.8 mW specified range and a peak output power at 40 nW with 8 nW specified range. The laser is pulsed at 25 ns and is timer controlled at 5 s or 10 s. The system 100 or the system 400 includes two types of laser fiber diameters at 200 micron and 300 micron, with a laser area of the tissue under treatment that is confined to the laser fiber diameter with less than 1 mm scatter.

The laser also operates on rechargeable batteries, does not require a dedicated power supply during operation, and is compatible with the North American 110-120 V/AC standard. The system 100 or the system 400 is also enclosed in a non-conducting insulated casing and does not require separate grounding during charging, operation, or both. In such implementations, because the laser has low output power, its use for pain treatment is safer than current deep tissue medical lasers with high intensity lasers.

The following sections describe an example DT-LILT procedure using the system 100 or the system 400 in some implementations. The DT-LILT procedure in these implementations does not involve use of sedation, general anesthetics, local anesthetics, or the use of oral or injectable drugs. The DT-LILT is performed bilaterally on the L5-S1 and L4-L5 face joints. During the procedure, a 25 G spinal needle is initially directed bilaterally at each of the L4-L5 and L5-S1 facet joints. Each facet joint is individually treated. Once the needle is embedded at the center of the facet joint, the laser fiber is inserted after removing the stylet. The DT-LILT generator is then switched on to deliver five seconds of laser energy.

In this manner, four facet joints are treated with one laser delivery point per facet joint with a five second laser delivery time and a 20 second total laser delivery time during the procedure. During the procedure, the patient is aware of the entire procedure to provide feedback. The patient may not feel discomfort other than from insertion of the needle.

During post procedure testing, which is performed to determine the effectiveness of the procedure in reducing or removing pain symptoms, pain resolution report from the patient is collected and the patient's ability to stand straight, flex the spine posteriorly are all evaluated. A Kemp test is also performed to assess the lumbar spine facet joints. A patient satisfaction score from a scale 0 to 100 (higher the score better the satisfaction) may be collected to determine pain reduction resulting from the procedure.

Results of test applications of DT-LILT indicated complete 100% resolution of pain symptoms after the procedure, with the patient able to stand straight and flex the spine posteriorly. The patient had negative Kemp test soon after the procedure. The patient also reported a satisfaction score of 100.

What is claimed is:

1. A system comprising:
a laser generator that is configured to generate a laser beam;
a spinal needle that is configured to be inserted into a human body for application of the laser beam; and
a laser fiber inserted within a hollow cavity of the spinal needle to a distal tip of the spinal needle, the laser fiber configured to transmit the laser beam from the laser generator to the distal tip of the spinal needle for application to the human body at a determined laser point,
wherein the laser generator is configured to generate a low intensity pulsed laser beam at a laser wavelength in a range between 690 nanometers to 710 nanometers with an average output power in a range between 1 milliwatts and 6 milliwatts and with a known pulse duration in a range of nano-seconds or pico-seconds, and
wherein the low intensity pulsed laser beam is configured to be applied to the human body at the determined laser point for a time interval between 5 seconds and 10 seconds.

2. The system of claim 1, wherein the pulse duration is 25 nano-seconds.

3. The system of claim 1, wherein the average output power includes 4 milliwatts with a range of +/−0.8 milliwatts around 4 milliwatts.

4. The system of claim 1, wherein the spinal needle includes one of a 22G or smaller spinal needle, or a 25G spinal needle with an inner diameter of 0.5 millimeters.

5. The system of claim 1, wherein the spinal needle includes a Quincke spinal needle.

6. The system of claim 1, wherein the laser fiber includes a diameter that is one of 200 microns, 300 microns, or is between 0.5 millimeters and 0.7 millimeters.

7. The system of claim 1, wherein the laser fiber is fixedly inserted within the hollow cavity of the spinal needle.

8. The system of claim 7, wherein the laser fiber is affixed to the spinal needle using a Luer lock mechanism.

9. The system of claim 1, further comprising a timer, wherein
the timer is configured with a preset time interval for application of the laser beam, wherein the preset time interval is between 5 seconds and 10 seconds.

10. The system of claim 1, wherein the low intensity pulsed laser beam applied to the human body at the determined laser point is configured to be absorbed by nerve cells causing non-thermal resonance of the nerve cells.

11. The system of claim 10, wherein application of the low intensity pulsed laser beam to the human body at the determined laser point comprises application of the low intensity pulsed laser beam using a specific pattern of laser beam contact with the nerve cells at lumbar spinal facet joints of the human body,
wherein the specific pattern is selected from the group consisting of 8 points in a circle around the facet joints; a continuous circle around the facet joints; 4 quadrants circled around the facet joints; a continuous cross pattern on the facet joints; continuous multiple cross patterns on the facet joints; multiple points forming a cross pattern on the facet joint; and multiple points forming multiple cross patterns on the facet joints.

12. A method comprising:
receiving, at a laser device, a user input inserting a spinal needle coupled to the laser device into a human body, wherein the spinal needle is positioned to contact a distal tip of the spinal needle with nerve cells;
receiving, at the laser device, a selection of a laser wavelength in a range between 690 nanometers and 710 nanometers;
generating, by the laser device, a low intensity pulsed laser beam at the selected laser wavelength with an average output power in a range between 1 milliwatt and 6 milliwatts and with a known pulse duration in a range of nano-seconds or pico-seconds;
transmitting, by the laser device, the laser beam through a laser fiber coupled to the laser device to the distal tip of the spinal needle; and
applying, by the laser device, the low intensity pulsed laser beam at the selected laser wavelength and with the known pulse duration to the nerve cells for a time interval between 5 seconds and 10 seconds.

13. The method of claim 12, wherein the selected laser wavelength and the known pulse duration are determined to:
induce absorption of the laser beam by the nerve cells; and
generate non-thermal nerve cell resonance of the nerve cells.

14. The method of claim 12, wherein generating the low intensity pulsed laser beam comprises:
operating a laser generator to provide the average output power in a range between 3.2 milliwatts and 4.8 milliwatts.

15. The method of claim 12, further comprising:
operating the laser generator to generate average output power of 4 milliwatts with a range of +/−0.8 milliwatts around 4 milliwatts.

16. The method of claim 12, wherein applying the low intensity pulsed laser beam for the time interval between 5 second and 10 seconds comprises:
operating a timer with a preset time interval for application of the laser beam, wherein the preset time interval includes one of 5 seconds or 10 seconds.

17. The method of claim 12, wherein generating the low intensity pulsed laser beam with the known pulse duration comprises:
generating the low intensity pulsed laser beam with a pulse duration of 25 nano-seconds.

18. The method of claim 12, wherein receiving the user input inserting the spinal needle coupled to the laser device into the human body comprises:
receiving a user input positioning the spinal needle at a particular laser point on the human body, wherein the particular laser point is determined for the application of the low intensity pulsed laser beam.

* * * * *

UNITED STATES PATENT AND TRADEMARK OFFICE
CERTIFICATE OF CORRECTION

PATENT NO. : 9,782,221 B2
APPLICATION NO. : 14/870327
DATED : October 10, 2017
INVENTOR(S) : Pattanam Srinivasan Page 1 of 1

It is certified that error appears in the above-identified patent and that said Letters Patent is hereby corrected as shown below:

Column 6, Line 42, Claim 15, after "generate" please insert --an--.

Signed and Sealed this
Nineteenth Day of December, 2017

Joseph Matal
*Performing the Functions and Duties of the*
*Under Secretary of Commerce for Intellectual Property and*
*Director of the United States Patent and Trademark Office*